US008908148B2

(12) United States Patent
Geraets et al.

(10) Patent No.: US 8,908,148 B2
(45) Date of Patent: Dec. 9, 2014

(54) CALIBRATION METHOD AND INSPECTION APPARATUS

(75) Inventors: Hubertus Antonius Geraets, Arendonk (BE); Gerardus Carolus Johannus Hofmans, Eindhoven (NL); Sven Gunnar Krister Magnusson, Warmbad-Villach (AT)

(73) Assignee: ASML Netherlands B.V., Veldhoven (NL)

( * ) Notice: Subject to any disclaimer, the term of this patent is extended or adjusted under 35 U.S.C. 154(b) by 635 days.

(21) Appl. No.: 13/181,905

(22) Filed: Jul. 13, 2011

(65) Prior Publication Data
US 2012/0013875 A1 Jan. 19, 2012

Related U.S. Application Data

(60) Provisional application No. 61/364,540, filed on Jul. 15, 2010.

(51) Int. Cl.
*G03F 7/20* (2006.01)
*G01N 21/93* (2006.01)
*G01N 21/956* (2006.01)

(52) U.S. Cl.
CPC ............ *G03F 7/70641* (2013.01); *G01N 21/93* (2013.01); *G01N 21/956* (2013.01); *G01N 2021/95676* (2013.01)
USPC .................... 355/55; 355/52; 355/53; 355/72; 355/77

(58) Field of Classification Search
CPC ............ G03F 7/70483; G03F 7/70516; G03F 7/70616; G03F 7/70625; G03F 7/70641; G03F 7/70591; G03F 7/706; G03F 7/7026; G03F 7/70258; G03F 7/0775; G03F 7/705
USPC ................. 355/52, 53, 55, 67–71, 72–74, 77; 250/492.1, 492.2, 492.22, 548; 430/5, 430/8, 22, 30, 311, 312
See application file for complete search history.

(56) References Cited

U.S. PATENT DOCUMENTS 5,191,200 A  3/1993  van der Werf et al.
6,081,614 A * 6/2000  Yamada et al. ............... 382/151

(Continued)

OTHER PUBLICATIONS

Charley, A.-L., et al., "Focus and dose de-convolution technique for improved CD control of immersion clusters", Proceedings of the SPIE—Metrology, Inspection, and Process Control for Microlithography XXIV, vol. 7638, pp. 763808-1 to 763808-8 (2010).

*Primary Examiner* — Toan Ton
*Assistant Examiner* — Christina Riddle
(74) *Attorney, Agent, or Firm* — Sterne, Kessler, Goldstein & Fox P.L.L.C.

(57) ABSTRACT

A method of calibrating an inspection apparatus. Obtaining a surface level measurements (LS) at respective level sensing locations LS(x,y). Determining focus settings ($LP_A$, $LP_B$) for exposure field regions ($EF_A$, $EF_B$) in accordance with surface level measurements ($LS_A$, $LS_B$) having level sensing locations corresponding to the respective exposure field region. Exposing exposure field regions ($EF_A$, $EF_B$) with focus offsets ($FO_1$, $FO_2$) defined with reference to the respective focus settings ($LP_A$, $LP_B$) to produce target patterns at respective target locations. Obtaining focus-dependent property measurements, such as Critical Dimension (CD) and/or side wall angle (SWA) of the target patterns measured using the inspection apparatus; and calibrating the inspection apparatus using the focus-dependent property measurements (CD/SWA) and the respective focus offsets ($FO_1$, $FO_2$). The calibration uses surface level measurements (e.g., $LS_B(3)$) having a level sensing location (e.g., $LSL_B(3)$) corresponding to the respective target location ($TL_B$). Each offset value is thus corrected in the calibration for the local wafer stack unflatness present during exposure.

10 Claims, 13 Drawing Sheets

(56) References Cited

U.S. PATENT DOCUMENTS

| | | | |
|---|---|---|---|
| 6,568,290 B1 * | 5/2003 | Poris | 73/866 |
| 6,944,578 B2 | 9/2005 | Bowley, Jr. et al. | |
| 7,042,551 B2 | 5/2006 | Ausschnitt | |
| 2003/0133088 A1 * | 7/2003 | Okita et al. | 355/53 |
| 2005/0132306 A1 * | 6/2005 | Smith et al. | 716/1 |
| 2005/0179880 A1 * | 8/2005 | Butler et al. | 355/53 |
| 2006/0050283 A1 * | 3/2006 | Hill | 356/512 |
| 2007/0105029 A1 * | 5/2007 | Ausschnitt | 430/30 |
| 2007/0135959 A1 * | 6/2007 | Vuong et al. | 700/121 |
| 2009/0153818 A1 | 6/2009 | Chauhan et al. | |
| 2009/0325087 A1 * | 12/2009 | Lyons | 430/30 |

\* cited by examiner ic # CALIBRATION METHOD AND INSPECTION APPARATUS

CROSS REFERENCE TO RELATED APPLICATIONS

This application claims benefit under 35 U.S.C. §119(e) to U.S. Provisional Application No. 61/364,540, filed Jul. 15, 2010, which is incorporated by reference herein in its entirety.

FIELD

The present invention relates to an inspection apparatus and a method for calibration of an inspection apparatus using a pattern produced with a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

Scanner focus can drift over time from the desired set point. Scanner stability feedback loops use measured critical dimension (CD) and side wall angle (SWA) to determine the wafer-level focus correction set for subsequent scanner exposures. To determine focus from CD and SWA, a calibration is performed, in an experiment where the focus is set with a range of offsets and measurements are made to obtain or "get" the CD or SWA. This is called a "set-get" experiment. One such set-get experiment is a focus exposure matrix (FEM). A FEM wafer may be used as calibration wafer for the scatterometer. As is known in the art, a FEM wafer comprises a wafer that has been coated with a photoresist onto which a pattern is exposed with multiple combinations of focus and exposure offsets. The FEM wafer is measured by the metrology tool to determine resist profiles, for example SWA, and line widths, for example CD, and the corresponding focus and exposure settings can be determined that most closely match a desired profile and line width.

In order to calibrate metrology tools used to control the focus of a lithography apparatus, it would be desirable to expose at specified offsets from a perfectly flat wafer plane, but in practice this is not the case. The wafer surface non-uniformity, or wafer stack unflatness, results in the actual focus set point across an exposure field being different from the intended focus set point FSP. This difference is the set point error. The local set point error may be large enough to cause poor definition of the exposed pattern in the resist. Wafer stack unflatness may be caused by a combination of wafer non-uniformity, wafer table non-uniformity and contamination between the wafer and the wafer table. In state of the art lithographic apparatus up to ±15 nm or even higher local stack unflatness may be observed. Focus set points are corrected to take into account the unflatness, by measuring and creating a leveling profile, which is the best height map to have the least leveling errors given the unflatness. When unflatness occurs on a scale smaller than the exposure field, however, then residual focusing errors will still occur in the exposure of the FEM wafer or other calibration target.

SUMMARY

It is desirable to accurately calibrate metrology tools that are used to measure focus-dependent properties of substrates.

According to a first aspect of the present invention, there is provided a method of calibrating an inspection apparatus, the method comprising: (a) obtaining a plurality of surface level measurements of a substrate at a plurality of different level sensing locations across the substrate, (b) determining a focus setting for an exposure field region in accordance with a plurality of the surface level measurements having level sensing locations corresponding to the field, (c) exposing the exposure field region on the substrate with a focus offset defined with reference to the focus setting to produce a pattern at a target location, (d) obtaining a focus-dependent property measurement (for example CD/SWA) of the pattern measured using an inspection apparatus, and (e) calibrating the inspection apparatus using the focus-dependent property measurement, the focus offset and at least one of the plurality of surface level measurements having a level sensing location corresponding to the target location.

According to a second aspect of the present invention, there is provided an inspection apparatus configured to measure at least one focus-dependent property measurement of pattern applied to a substrate by projection lithography, and to report a focus property of the pattern based on the focus-dependent property measurement and a calibration curve, wherein the calibration curve has been obtained by measuring the focus-dependent property at a plurality of locations on a calibration substrate, each of the locations falling within an exposure field on which a calibration pattern has been applied with a known focus offset across the field, and wherein the calibration curve has been obtained taking into account not only the focus offset associated with the exposure field, but also taking into account local focus deviations caused by unflatness of the substrate surface within the field at a time of exposing the calibration pattern.

According to a third aspect of the present invention, there is provided a lithographic apparatus comprising: an illumination optical system arranged to illuminate a patterning device, a projection optical system arranged to project an image of the patterning device on to a substrate, and an inspection apparatus according to the second aspect of the present invention, as set forth above.

According to a fourth aspect of the present invention, there is provided a lithographic cell comprising: a coater arranged to coat substrates with a radiation sensitive layer, a lithographic apparatus arranged to expose images onto the radiation sensitive layer of substrates coated by the coater, a developer arranged to develop images exposed by the lithographic apparatus, and an inspection apparatus according to the second aspect of the present invention, as set forth above.

According to a fifth aspect of the present invention, there is provided a computer program product containing one or more sequences of machine-readable instructions for calibrating an inspection apparatus, the instructions being adapted to cause one or more processors to perform a method of calibrating an inspection apparatus, the method comprising the steps: obtaining a plurality of surface level measurements of a substrate at a plurality of different level sensing locations across the substrate, determining a focus setting for an exposure field region in accordance with a plurality of the surface level measurements having level sensing locations corresponding to the field, obtaining a focus-dependent property measurement of a pattern measured using an inspection apparatus, the pattern produced at a target location by a lithographic apparatus exposing the exposure field region on the substrate with a focus offset defined with reference to the focus setting, and calibrating the inspection apparatus using the focus-dependent property measurement, the focus offset and at least one of the plurality of surface level measurements having a level sensing location corresponding to the target location.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
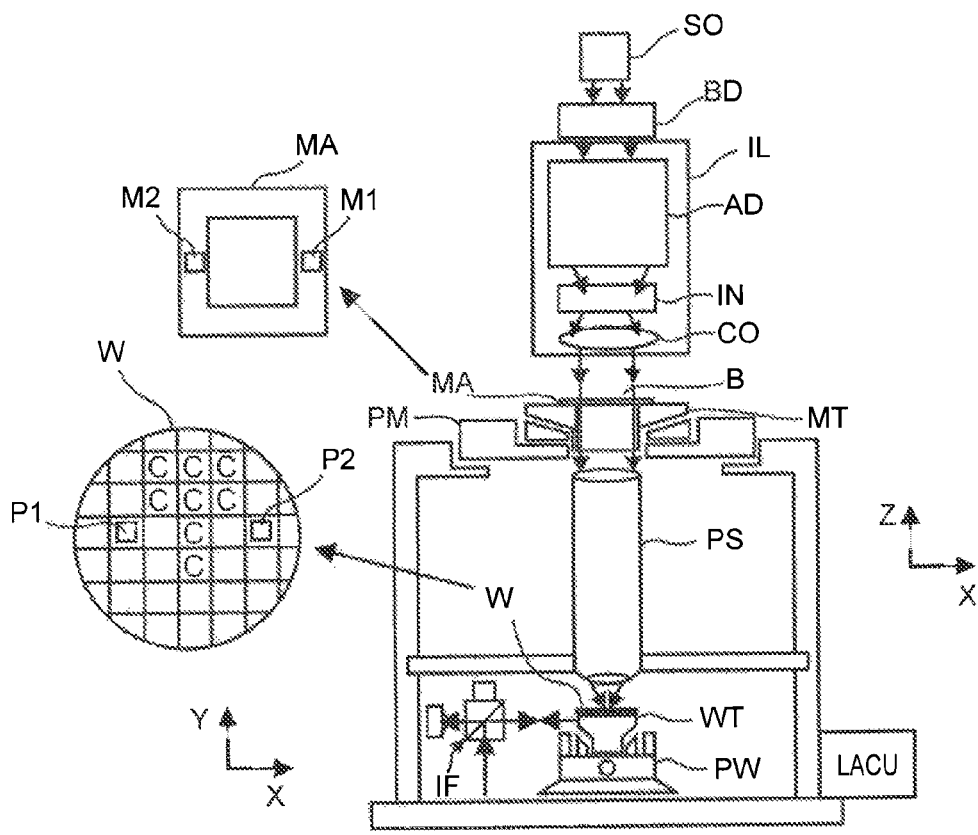
FIG. 1 depicts a lithographic apparatus, according to an embodiment of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus according to one embodiment of the present invention. The apparatus comprises an illumination system (illuminator) IL configured to condition a radiation beam B (e.g., UV radiation or Extreme UV (EUV) radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
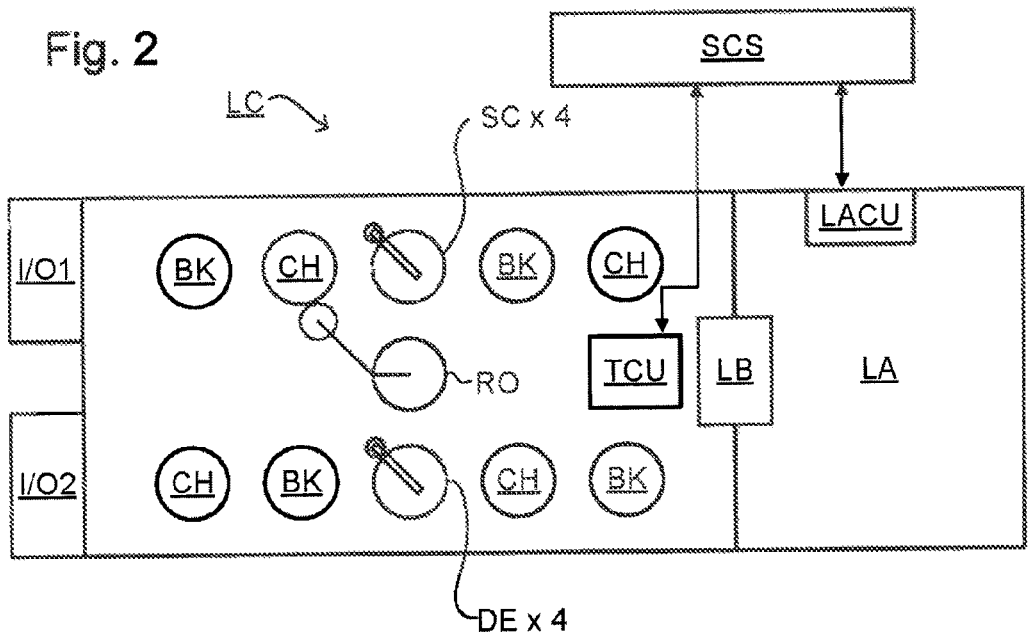
FIG. 2 depicts a lithographic cell or cluster including the apparatus of FIG. 1.

FIG. 2 depicts a lithographic cell or cluster including the apparatus of FIG. 1. As shown in FIG. 2, the lithographic apparatus LA forms part of a lithographic cell LC, also sometimes referred to a 'lithocell' or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Figure 3:
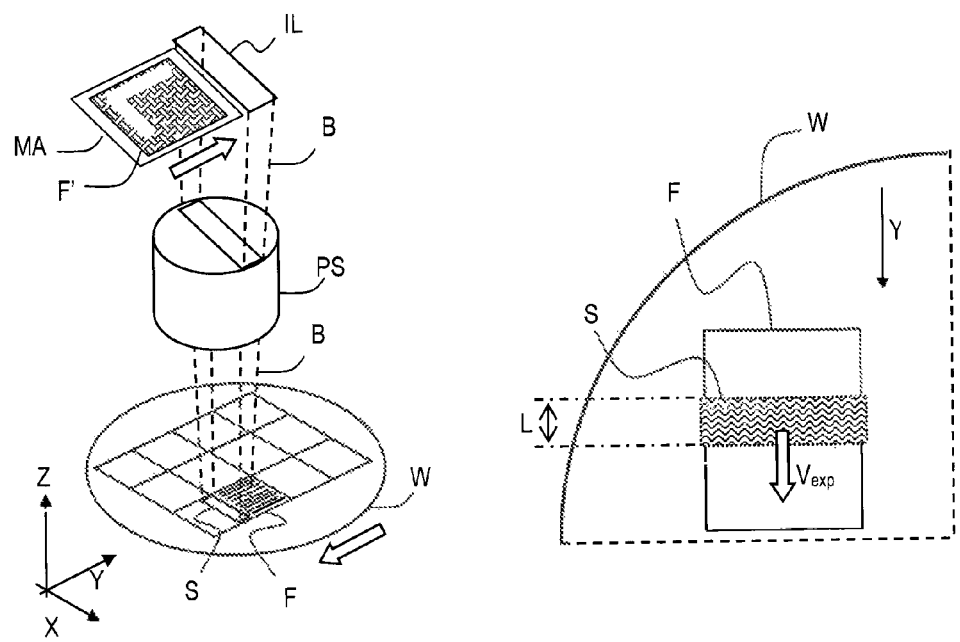
FIG. 3 illustrates schematically the operation of the apparatus of FIG. 1 in exposing a target portion (field) on a substrate.

FIG. 3 illustrates schematically the scanning operation to expose one field F on a substrate W in the lithographic apparatus of FIG. 1. The substrate W and mask MA are seen in perspective view, with the illumination source IL above and the projection system PS in between. Mask MA carries a transparent pattern F' which is a scaled up version of the pattern to be applied to one field F on substrate W. Illumination source IL presents a slit of radiation S', not large enough in the Y direction to cover the area F' but wide enough in the X direction. To expose the entire field, the mask MA is moved through the area of slit S' to project a corresponding slit area S on substrate field F. These movements are represented by large arrows.

Conceptually, it is sufficient to regard the substrate as staying still, while the patterned slit S passes over it in the opposite sense of the Y direction, as shown by the schematic plan detail to the right of the diagram. The slit with length L is moved with an exposure velocity Vexp over field F.

Parameters of the projection system PS and control set points are adjusted prior to exposure to ensure that distortion within the slit is constant over the whole exposure. Certain parameters, for example focus set points, may be controlled dynamically throughout the scanning movement, to maintain optimum, uniform patterning quality across the field.

Figure 4:
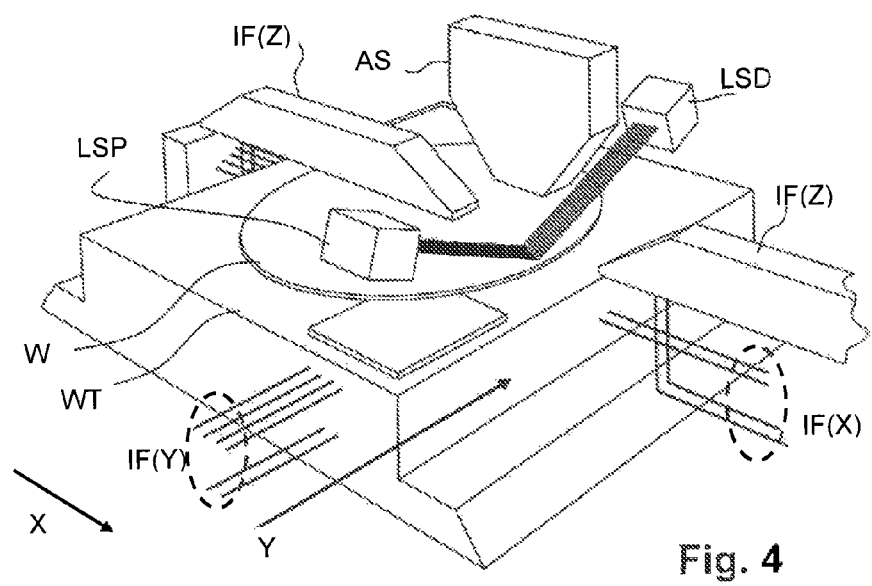
FIG. 4 illustrates a level sensor apparatus in the lithography apparatus of FIG. 1.

FIG. 4 is a perspective view of level mapping operations taking place in a known lithographic apparatus. Substrate table WT is shown with a substrate W loaded thereon which is being measured by a level sensor comprising a level sensing projector LSP and a level sensing detector LSD. An alignment sensor AS is provided for measuring X-Y position across the substrate. Position sensor IF, seen in FIG. 1, is seen in more detail in FIG. 4. A pair of Z-direction position sensors IF(Z) are provided (in this example, interferometers), while IF(X) represents rays of the X-direction interferometer, and IF(Y) represents rays of the Y-direction interferometer. As mentioned previously, other forms of position sensor may be used, for example, encoder plates, as is known to the skilled person.

In operation of the known level sensor, a number of level sensing "spots" are projected onto a line-shaped portion of the substrate surface, by projector LSP, and reflected from the substrate surface to be imaged in the level sensing detector LSD.

Figure 5:
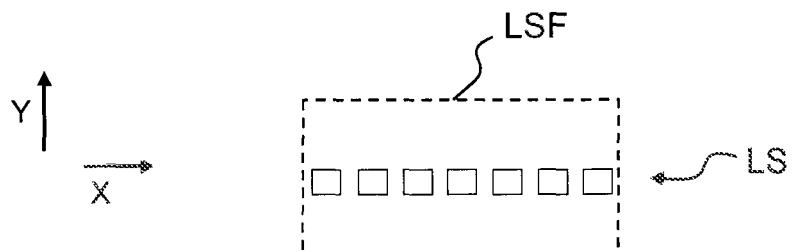
FIG. 5 illustrates level sensor measurement spots across a level sensing field.

FIG. 5 shows a row of seven levels sensing spots LS within a level sensing field LSF, as projected onto the wafer. Each spot LS may comprise a pattern of lines created by an array of slits in the projector. This array of slits will be referred to as a 'grating' for simplicity. The array of slits are spaced more widely than a wavelength of the sensing radiation, so the term 'grating' is not used here in the sense of a diffraction grating. In principle, a simple spot could be used, but the use of multiple lines, increasing the number of edges in the dimension to be sensed, improves measurement performance. The spot in this example is shaped in the projected beam so as to cover a roughly square patch on the substrate W. The patch may be, for example, 2-3 mm square, the size and shape of the spot being chosen according to the desired performance. The line of spots may cover, for example, a 30 mm strip of substrate surface, with the substrate W being for example 300 mm in diameter. A scanning motion of substrate table WT in the Y-direction is used to map surface levels along a stripe of the substrate before stepping to the next X-position. Because motion of the stage WT is linear during measurement, there are no acceleration forces to distort the table or substrate and disturb the measurements. Level sensor projector LSD and detector LSP in the known apparatus are based on one of the embodiments described in U.S. Pat. No. 5,191, 200, which is incorporated by reference herein in its entirety.

Figure 6:
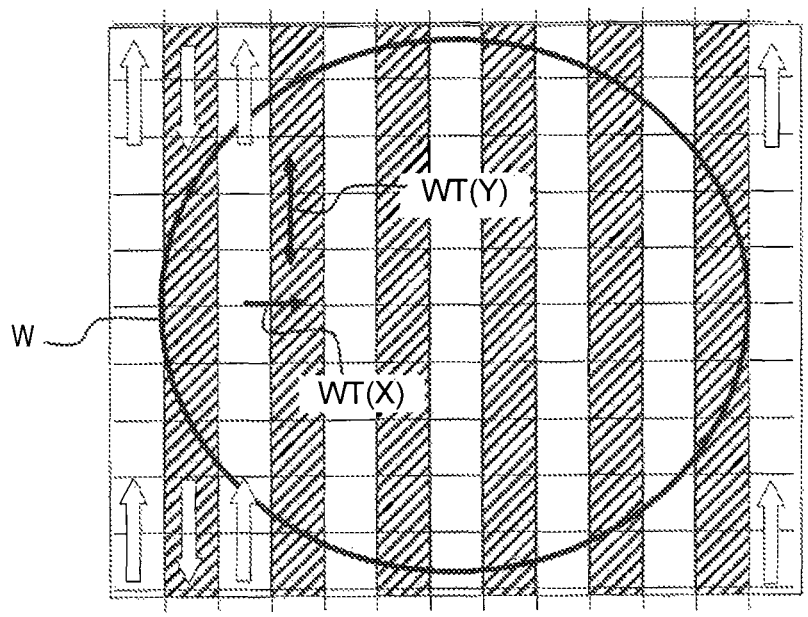
FIG. 6 illustrates a scanning pattern of level sensing fields that may be implemented in the known level sensor.

FIG. 6 illustrates the form of a scanning pattern that may be implemented to cover a target substrate W. The bold circle represents the area of substrate W. FIG. 6 illustrates the operation of the apparatus of FIG. 4, in which scanning in the Y-direction is performed by moving the substrate support WT beneath the sensors, and stripes corresponding in width to the field areas (target portions C) are measured, stepping in the X-direction between stripes. Alternate stripes covered by the sensor are shaded, with open arrows indicating the path of the level sensing spot array across the substrate. Each stripe may be scanned multiple times by the sensor to improve accuracy, in which case the open arrows shown might all point in the same direction, rather than alternating directions. Such details of implementation can be readily worked out by the skilled reader.

Figure 7:
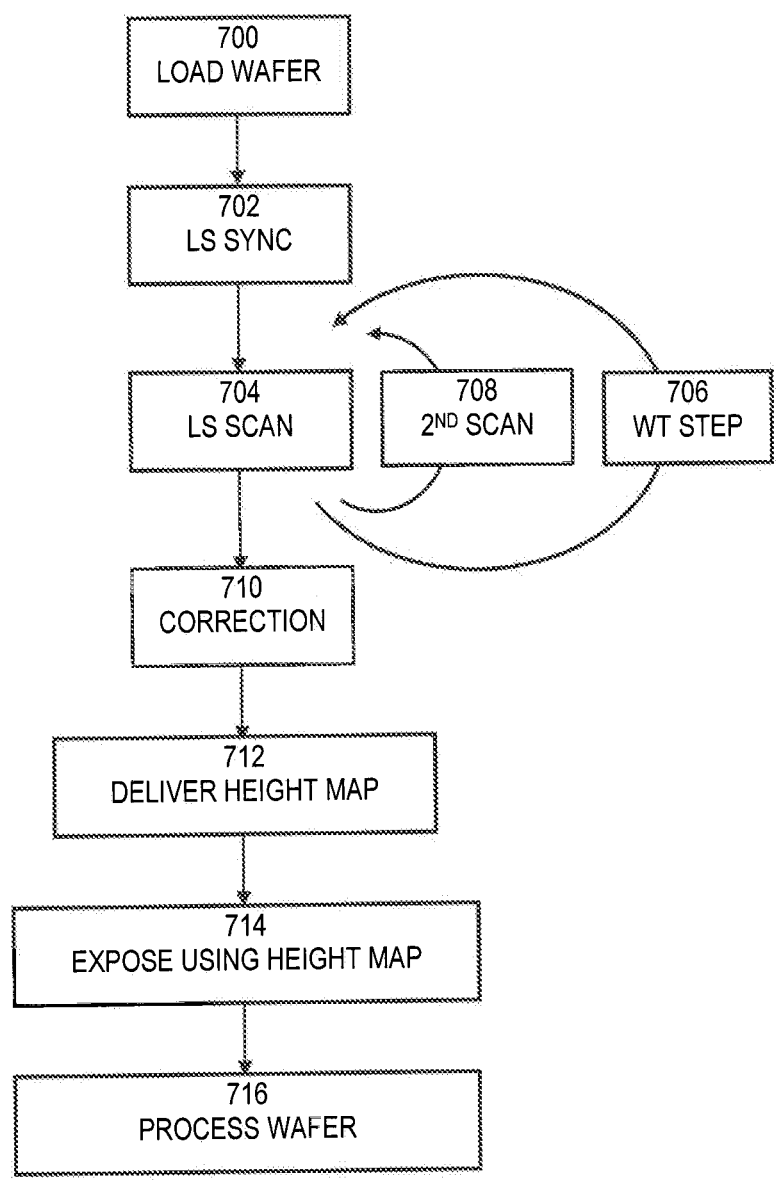
FIG. 7 illustrates a level sensing and product manufacturing process using the scanning level sensor of FIG. 4.

FIG. 7 provides an overview of the level scanning process using the scanning level sensors of FIG. 4. At 700 a substrate (wafer etc) is loaded into a lithography apparatus. At 702 the level sensing apparatus is started. At 704 a stripe of the target is presented and scanned by the moving spot or spot array. At 706 the substrate table is stepped in the direction perpendicular to the scanning stripe, and/or is subject to continuous scanning movement in the direction, and the scan of the next stripe is performed by a repeat of step 704. Optionally as described above, step 708 may involve setting height setpoint profile and/or other servo parameters of the level sensors and performing a second scan with increased accuracy and reduced sensitivity to wafer tilt etc. The second scan may be of the same stripe, in which case no movement in the X direction is made between the first and second scan. Alternatively, the measured height profile may be used to improve scanning in an overlapping stripe or a neighboring but non-overlapping stripe. Depending on the shape of the wafer and the scale of each measurement, measurements made in a neighboring stripe may serve as a good predictor of the profile in a current stripe. This predictor can be used as a reference to adjust the height set point profile of the sensor when scanning the current stripe. The measurement of a neighboring stripe can in particularly be useful as a predictor to reduce height servo errors in the 'scan in' phase at the beginning of a current scan.

At 710 any corrections such as for lens aberrations are applied, prior to delivering the finished height map at 712. While the steps 704, 710, 712 are shown sequentially, all or part of the corrections may be during the scanning measurements. The height map may be delivered in one go to a controller for the subsequent exposure operation, or it may be provided as a stream, while scanning is still in progress. At 714 the product patterns from patterning device MA (FIG. 1) are exposed onto the target portions C (fields) of substrate W, using the height map obtained from the level sensor to maximize focus accuracy of the projected pattern at every portion and, in the case of a scanning exposure, during exposure of each portion. At 716, the exposed substrate is processed in a well-known manner to create actual product features on the substrate. The entire process may be repeated to produce a multi-layer device, as is well known.

Figure 8:
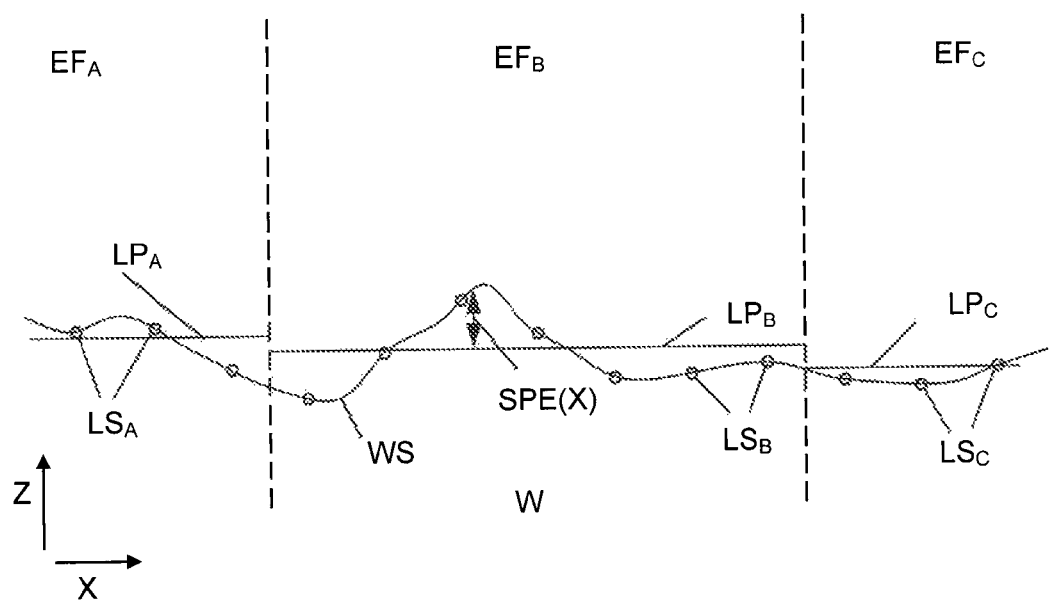
FIG. 8 illustrates level sensor measurements of wafer stack unflatness being used to calculate a leveling plane.

FIG. 8 illustrates level sensor measurements of wafer stack unflatness being used to calculate a leveling plane LP. The leveling plane LP is a varying plane through the height map followed by the stage as it moves through each exposure field. The leveling plane LP determined from the leveling sensor measurements at a particular Y position in an exposure field on the wafer is used to determine the set point for the scanner for exposure at the exposure field region at that Y position in the exposure field. The leveling plane LP is therefore a focus setting for the exposure at the exposure field region in the respective exposure field. The leveling plane at any Y position is determined in accordance with the surface level measurements having level sensing locations corresponding to the respective exposure field region. In FIG. 8, the height in the Z direction of the wafer W surface WS is plotted in the X direction for a level sensing field at a particular X and Y position. The seven level sensor measurements LSB in the exposure field region EFB are used to calculate a leveling plane LPB for that exposure field region. The leveling plane LP may be calculated using for example linear regression. In FIG. 8, the leveling planes LP are shown as being a horizontal lines, but they could also be sloping lines, if the focus correction mechanism allows a tilted focus set point for the exposure field, or curved lines if the focus correction mechanism allows a non-linear set point across the field. The focus set point FSPB is defined using the leveling plane LPB, such that the average set point error SPE(X) across the field is zero. This leads to improved pattern definition as the focus set point FSPB is closer to the actual focus set point AFSP(X), on average across the field.

The leveling planes in adjacent exposure fields are calculated separately, based on level sensor measurements in their respective fields. For example, at the left side of FIG. 8, part of EFA is shown, with three of the seven level sensor measurements and the calculated leveling plane LPA for that exposure field EFA. Similarly, at the right of FIG. 8, part of EFB is shown, with the calculated leveling plane LPB for that exposure field region EFB. In the same way, it should be appreciated that wafer surface height variation in the Y direction, will result in level sensing fields in different Y positions (not shown) having different level sensor measurements and leading to a calculated leveling plane that is moving in the Y direction.

The discussion of FIGS. 4 to 8 above has introduced the problem of wafer stack unflatness and the use of level sensing to mitigate its effects in lithography using a scanner. Wafer stack unflatness can also cause problems with the calibration of inspection and metrology tools for monitoring the lithographic process, as will now be discussed.

In order that the substrates that are exposed by the lithographic apparatus are exposed correctly and consistently, it is desirable to inspect exposed substrates to measure properties such as line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus or metrology tool is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

A key component of accurate lithography is an ability to calibrate individual lithographic apparatus. In addition to general parameters affecting the whole substrate area, it is known to map and model the error 'fingerprint' of an individual apparatus across the substrate area. This fingerprint, which can be established in terms of focus, dose and/or alignment, can be used during exposure to correct the idiosyncrasies of that apparatus, and thereby achieve a more accurate patterning.

Improvements to the apparatus's focus and overlay (layer-to-layer alignment) uniformity have recently been achieved by the applicant's Baseliner™ scanner stability module, leading to an optimized process window for a given feature size and chip application, enabling the continuation the creation of smaller, more advanced chips. The scanner stability module may automatically reset the system to a pre-defined baseline each day. To do this it retrieves standard measurements taken from a monitor wafer using a metrology tool. The monitor wafer is exposed using a special reticle containing special scatterometry marks. From that day's measurements, the scanner stability module determines how far the system has drifted from its baseline. It then calculates wafer-level overlay and focus correction sets. The lithography system then converts these correction sets into specific corrections for each exposure on subsequent production wafers.

Figure 9:
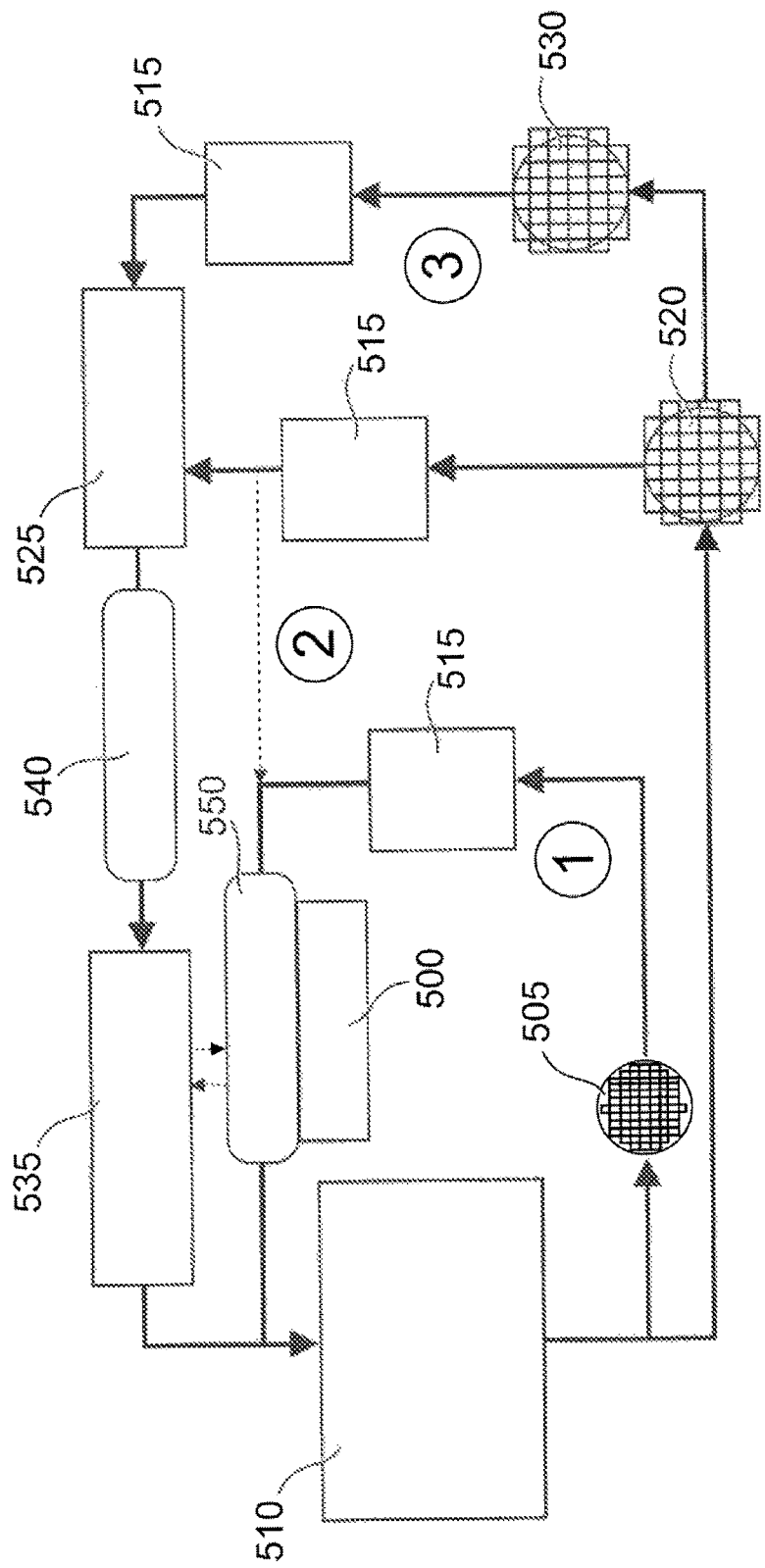
FIG. 9 is a schematic diagram of control mechanisms in a lithographic process utilizing a scanner stability module.

FIG. 9 depicts the overall lithography and metrology method incorporating the scanner stability module 500 (essentially an application running on a server, in this example). Shown are three main process control loops. The first loop provides the local scanner control using the scanner stability module 500 and monitor wafers. The monitor wafer 505 is shown being passed from the main lithography unit 510, having been exposed to set the baseline parameters for focus and overlay. At a later time, metrology tool 515 reads these baseline parameters, which are then interpreted by the scanner stability module 500 so as to calculate correction routines so as to provide scanner feedback 550, which is passed to the main lithography unit 510, and used when performing further exposures.

The second Advanced Process Control (APC) loop is for local scanner control on-product (determining focus, dose, and overlay). The exposed product wafer 520 is passed to metrology tool 515 where information relating to the critical dimensions, sidewall angles and overlay is determined and passed onto the Advanced Process Control (APC) module 525. This data is also passed to the scanner stability module 500. Process corrections 540 are made before the Manufacturing Execution System (MES) 535 takes over, providing scanner control to the main lithography unit 510, in communication with the scanner stability module 500.

The third loop is to allow metrology integration into the second APC loop (e.g., for double patterning). The post etched wafer 530 is passed to metrology tool 515 which again passes information relating to the critical dimensions, sidewall angles and overlay, read from the wafer, to the Advanced Process Control (APC) module. The loop continues the same as with the second loop.

Figure 10:
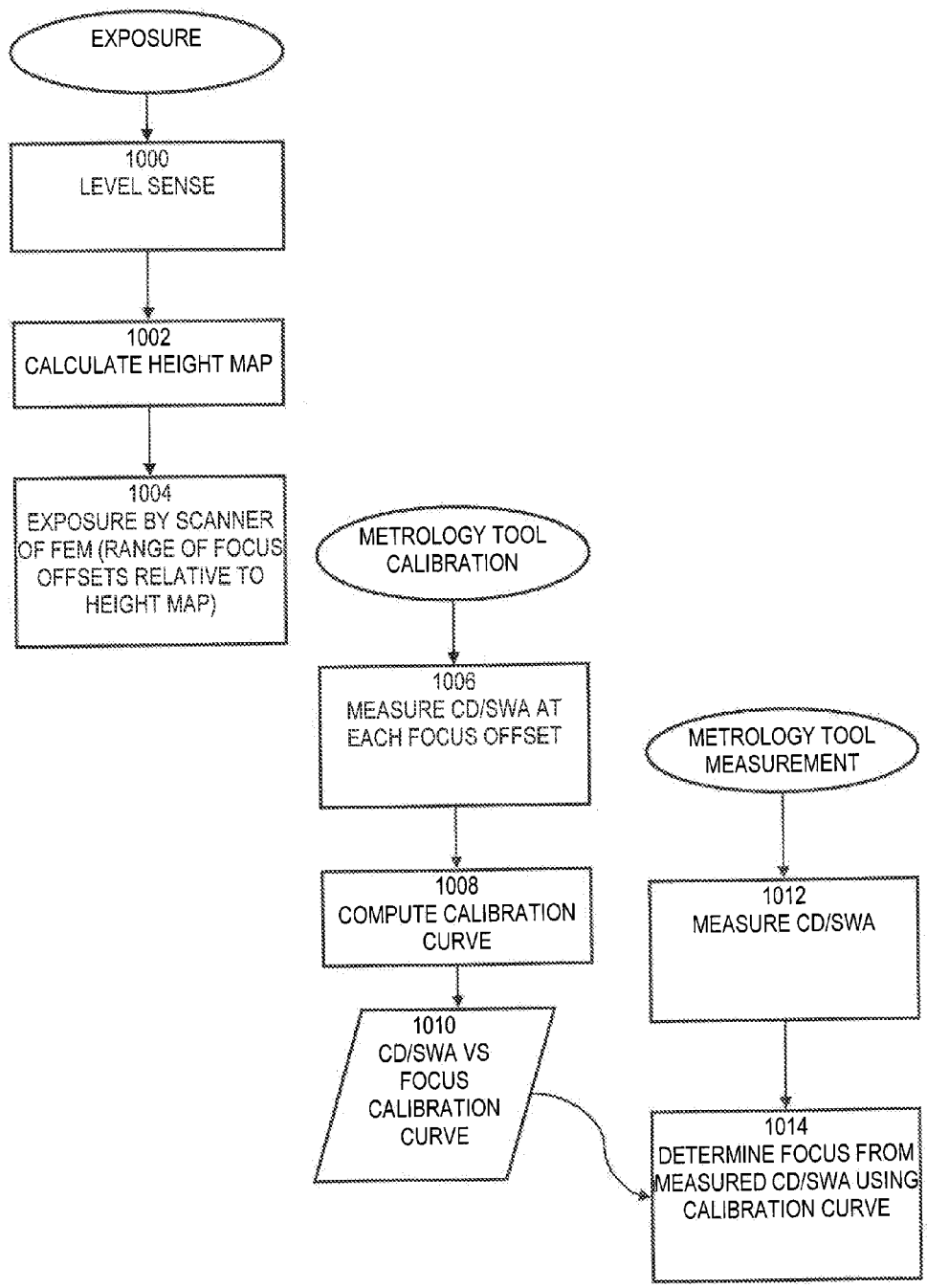
FIG. 10 is a flow chart of metrology tool calibration and measurement.

FIG. 10 is a flow chart of inspection apparatus (metrology tool) calibration and measurement. In the exposure process, the level sensing measurement is performed 1000, as described with reference to FIGS. 5 and 6 above, to obtain wafer surface level measurements at respective locations across the exposure fields on a calibration wafer.

The height map consisting of leveling planes LP for each field is calculated 1002, as described with reference to FIG. 8 above.

Exposure fields regions on the calibration wafer are exposed 1004 with a range of focus offset FO defined with reference to the respective leveling plane LP. This produces target patterns at target locations on the calibration wafer.

For calibration of the metrology tool, a focus-dependent property of each target pattern, such as the CD and/or SWA, is obtained by measurement 1006 using the metrology tool to be calibrated, for example a scatterometer or CD-SEM (scanning electron microscope).

The calibration is computed 1008 by storing focus offsets with corresponding measured CD and/or SWA in a table, then calculating the response function of CD and/or SWA with respect to focus, for example using linear regression. This resulting CD and/or SWA versus focus calibration data 1010 is thus generated. The calibration data 1010 of FIG. 10 may be simply the parameters of a fitted curve, such as a line's slope and intercept. Alternatively, the calibration data 1010 may be provided as raw data in the table.

The right-hand side of FIG. 10 shows a subsequent measurement using the calibrated metrology tool. This may be performed for example in the monitor process corresponding to the first process control loop of FIG. 9, using measurement of monitor wafers 505 and the scanner stability module 500 for feedback of measurements. The CD and/or SWA are measured 1012 using the metrology tool. Using the calibration data or curve 1010, the focus is determined 1014 from the measured CD and/or SWA.

Figure 11:
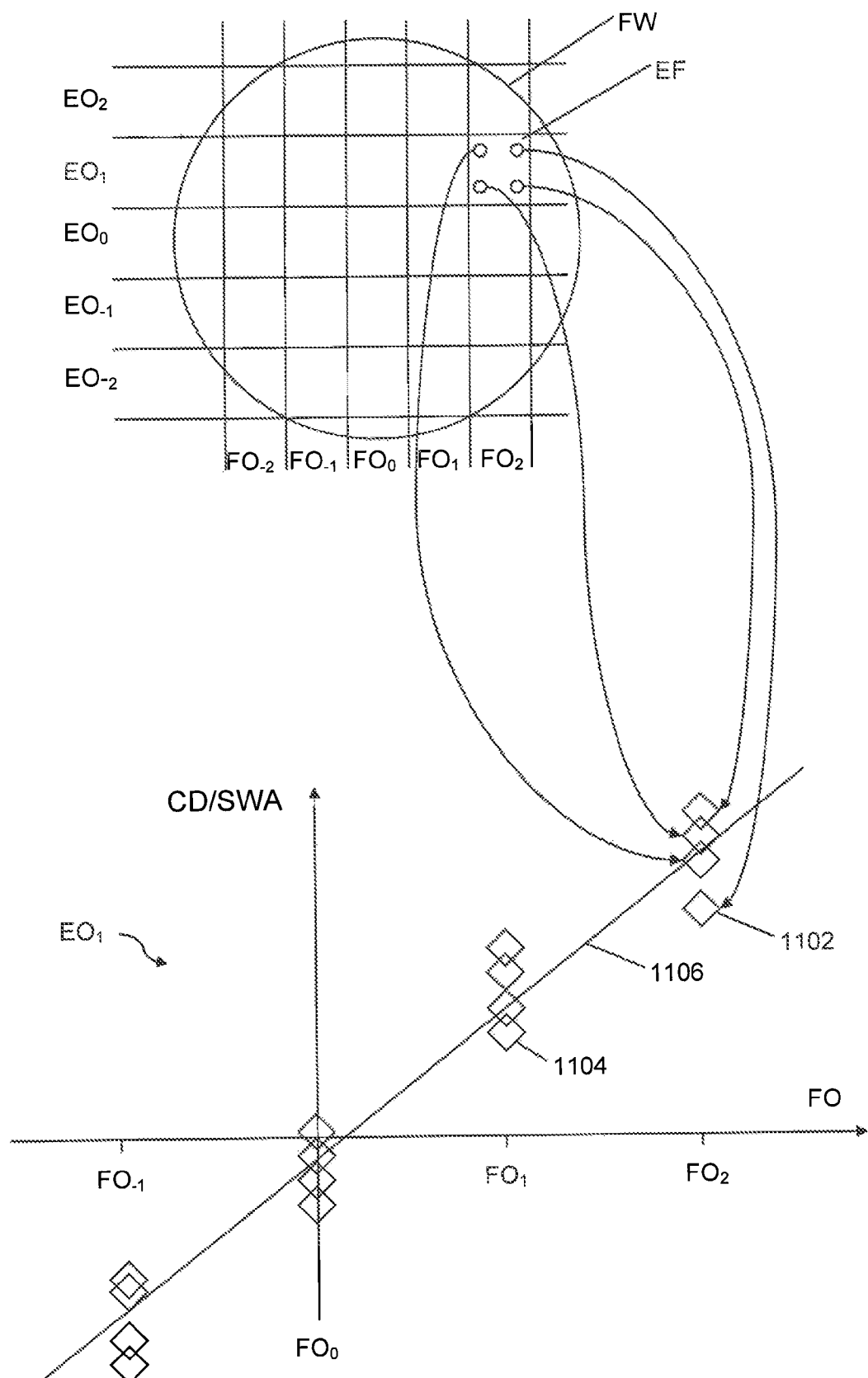
FIG. 11 illustrates a focus exposure matrix for metrology tool calibration and a graph of results of critical dimension (CD) or side wall angle (SWA) versus focus offset (FO).

FIG. 11 illustrates a focus exposure matrix (FEM) on a calibration wafer for metrology tool calibration and illustrates a graph of measurement results plotted with critical dimension (CD) or side wall angle (SWA) on the vertical axis and focus offset (FO) on the horizontal axis. In FIG. 11, the FEM has a matrix of exposure fields, for example EF. Each column in this example has a different focus offsets, FO-2 to FO2. The top row is exposed at an exposure offset EO2 and the next row down is exposed with an exposure offset EO1 and so on. It will be apparent to the skilled person that there may a variable number of exposure offsets and focus offsets and that the layout of the exposure sites on the wafer may be randomized to mitigate systematic cross-wafer effects.

The measured values of CD or SWA, e.g., 1102 and 1104 are used to determine a relationship between focus and CD or SWA, for example by linear regression. This is shown graphically in FIG. 11, where a calibration curve 1106 is fitted to the data points to obtain the response function of CD or SWA with respect to focus. In this simple example, and in the graph in FIG. 14, a straight line calibration curve is shown, but in practice the calibration curve will be a curve with polynomial coefficients.

A subset of the measured CD or SWA measurements has been selected for presentation in FIG. 11, all having the exposure offset EO1. A plurality of focus measurements, for example the four small circles in field EF are performed in field EF in the FEM. The measurements are used to obtain the calibration curve as indicated by the arrows joining the small circles to the respective data points on the graph of FIG. 11.

Variation in the measured CD/SWA for a given focus offset FO1, FO2, etc., caused by wafer stack unflatness, spreads the data along the vertical axis. This results in uncertainty in the fitting of the calibration curve 1106, for example giving large residuals in the curve fitting.

Figure 12:
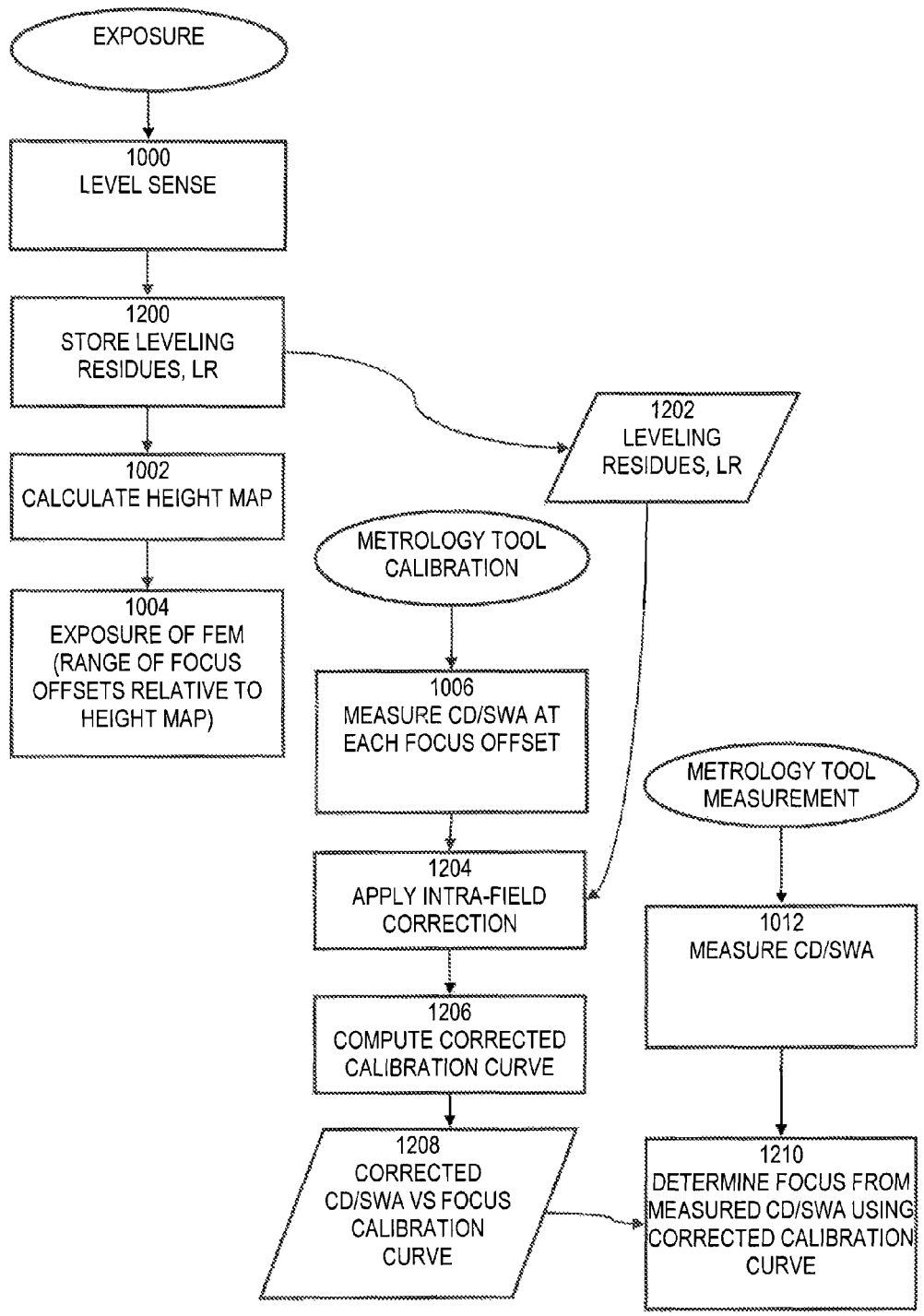
FIG. 12 is a flow chart of metrology tool calibration and measurement, according to an embodiment of the present invention.

FIG. 12 is a flow chart of inspection apparatus calibration and focus measurement according to an embodiment of the present invention. Steps that are the same as FIG. 10 are labeled identically. However, in FIG. 12, the leveling residues LR, which are the differences of each level sensor measurement from the determined respective leveling plane, are stored 1200. The leveling residue LR data 1202 are passed from the scanner to a metrology tool calibration apparatus or calibration unit, which may be integrated into the metrology tool, or may be for example a separate hardware or software module. The leveling residue LR data 1202 is used after measurement of the CD/SWA by a calibration unit in a metrology tool to apply 1204 intra-field correction in the calibration. This may be performed for example by storing focus offsets with corresponding measured CD and/or SWA in a table, along with the leveling residues LR that have level sensing locations corresponding to the respective locations on the wafer where the CD and/or SWA were measured on the focus targets. For each row in the table, the leveling residues LR may be subtracted from the respective focus offset FO to apply the intra-field focus correction 1204. This is described below with reference to FIG. 13. Then the corrected response function (calibration curve) of CD and/or SWA with respect to focus is calculated 1206 and stored as calibration data 1208. The calibration data may alternatively comprise raw data for use to convert subsequent CD and/or SWA measurements to focus.

Thus the calibration uses the measured CD and/or SWA of the focus targets, the focus offsets FO and surface level measurements LS that have a level sensing location on the wafer corresponding to the respective focus target location on the wafer.

Similarly to FIG. 10, the right-hand side of FIG. 12 shows the measurement using the calibrated metrology tool. The CD and/or SWA are measured 1012 using the metrology tool. Using the corrected calibration data 1208, the focus is determined 1210 from the measured CD and/or SWA.

Figure 13:
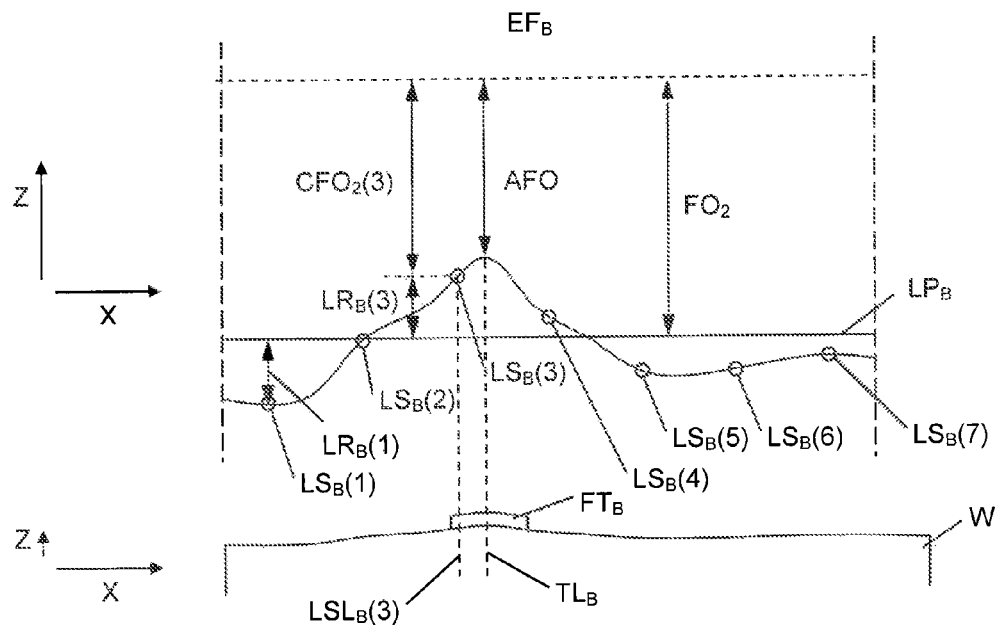
FIG. 13 illustrates level sensor measurements of wafer stack unflatness being used to calculate a leveling plane and further illustrates the definition of leveling residues and a corrected focus offset.

FIG. 13 illustrates level sensor measurements of wafer stack unflatness in a level sensor field being used to calculate a leveling plane and the definition of leveling residues and a corrected focus offsets. FIG. 13 illustrates one exposure field region EFB with the seven level sensor measurements LSB(1) to LSB(7) being used to calculate a leveling plane LPB. The leveling residues LRB(1) to LRB(7) are the differences of each level sensor measurement LSB(n) from the determined respective leveling plane LPB. The corrected focus offset CFO2 is obtained by subtracting the level sensor residue LRB(3) from the focus offset FO2 from the leveling plane LPB. That particular level sensor residue is chosen because it has a level sensing location LSLB(3) corresponding to the focus target location TLB.

Thus, the corrected focus offset used for the calibration may be expressed as:

$$CFO_2 = FO_2 - LR_B(3) = FO_2 - (LS_B(3) - LP_B)$$

Each offset value is thus corrected in the calibration for the local wafer stack unflatness present during exposure.

Figure 14:
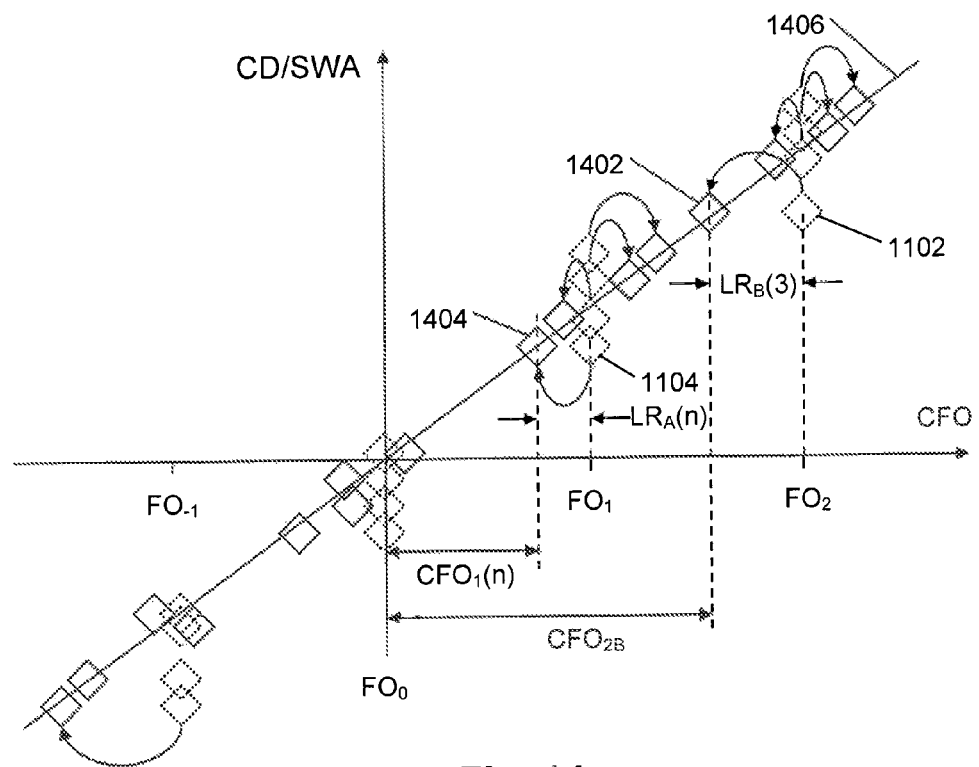
FIG. 14 is a graph of results of critical dimension (CD) or side wall angle (SWA) versus corrected focus offset, in accordance with an embodiment of the present invention.

FIG. 14 is a graph of results of critical dimension (CD) or side wall angle (SWA) versus corrected focus offset in accordance with an embodiment of the present invention. The vertical graph axis is the same as for the graph in FIG. 11, however, the horizontal axis is instead the corrected focus offset CFO. The dotted diamonds, for example 1102 and 1104, are the same points as shown in FIG. 11, that is with the uncorrected focus offset as the horizontal axis. The effect of applying the intra-field focus correction by correcting the focus offset values FO2 and FO1 with their corresponding local leveling residue LRB(3) and LRA(n) respectively is apparent as a horizontal shift of each data point from the dotted diamonds, for example 1102 and 1104, to respective solid diamonds, for example 1402 and 1404. It can be seen that the solid diamonds lie closer to an expected straight line calibration curve CC.

When the data shown in FIG. 14 is used to obtain the calibration curve response of CD or SWA to focus, for example by linear regression, then a better fit, with smaller residuals, is obtained. This has the effect of higher calibration accuracy of the metrology tool. The higher accuracy has the effect that fewer exposures need to be made in FEM wafers, therefore less exposure time is needed and less time for measurement is also required.

The higher accuracy is also beneficial when simple focus set-get procedures are used, sometimes referred to as "process flags" or inline stability markers In this technique, a tilted focus field is used with positive and negative focus offsets, such as FO-1 and FO1 in FIG. 14. These focus offsets (small relative to the range of offsets used in a FEM) are more sensitive to the smearing in the vertical axis shown in FIG. 11, cause by intra-field unflatness. The correction of the leveling residues in calibrating the measurement of inline stability markers therefore gives a relatively larger improvement in calibration accuracy.

Figure 15A:
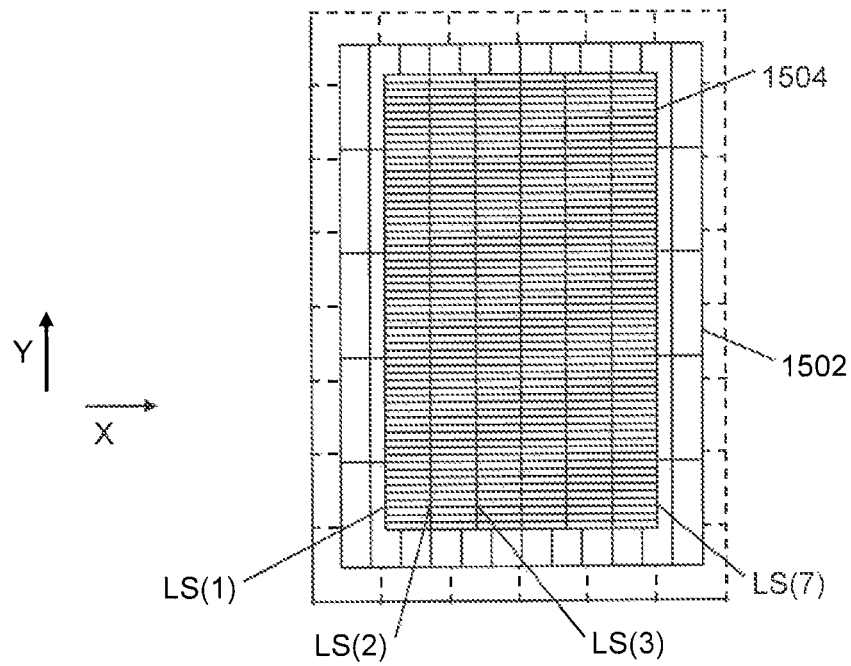
FIG. 15a illustrates one exposure field with the FEM pattern grid overlaid with the level sensing map grid.
Figure 15B:
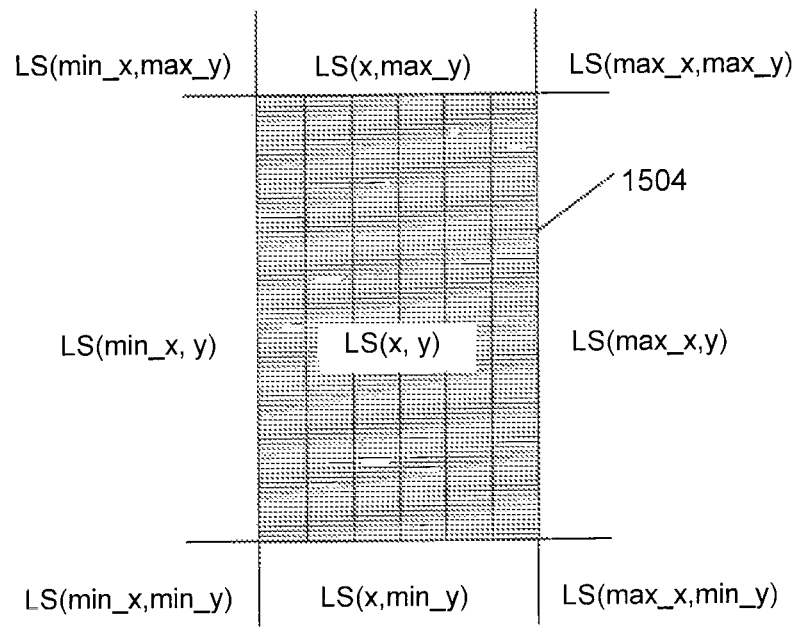
FIG. 15b illustrates the level sensing map grid with values extrapolated outside the grid.

FIGS. 15a and 15b illustrate one way of relating the level sensing locations to the target locations. It should be appreciated that there are other ways to achieve this. FIG. 15a illustrates one exposure field with the FEM pattern grid overlaid with the level sensing map grid. The FEM grid 1502 is a grid of locations of patterns with varying settings, including focus offsets. The level sensing height map grid 1504 is overlaid. The seven level sensing locations are at the intersections of the lines on the grid 1504, and as an example LS(1), LS(2), LS(3), and LS(7) are labeled.

The intra-field level sensing corrections are used on the FEM grid 1502. For all FEM grid points inside the level sensing grid 1504 the corrections on the FEM grid may be obtained by a linear interpolation of the data on the level sensing grid LS(x,y). Because the grid of the level sensing map 1504 does not cover the full FEM grid 1502 for all fields, it may be necessary to extend the level sensing map data to the FEM grid points outside of the measured area. The values on the FEM grid outside of the level sensing grid are obtained by extrapolating the values on the level sensing grid LS(x,y). An extrapolation method illustrated by FIG. 15b assigns the value of the closest point within the level sensing grid to the point outside of the level sensing grid. This means that the level sensing values outside of the level sensing grid 1504 are set equal to those on the nearest edge of the level sensing grid (defined by min_x, max_x, min_y, and max_y), for example LS(max_x,y) at the center right of FIG. 15b.

Figure 16:
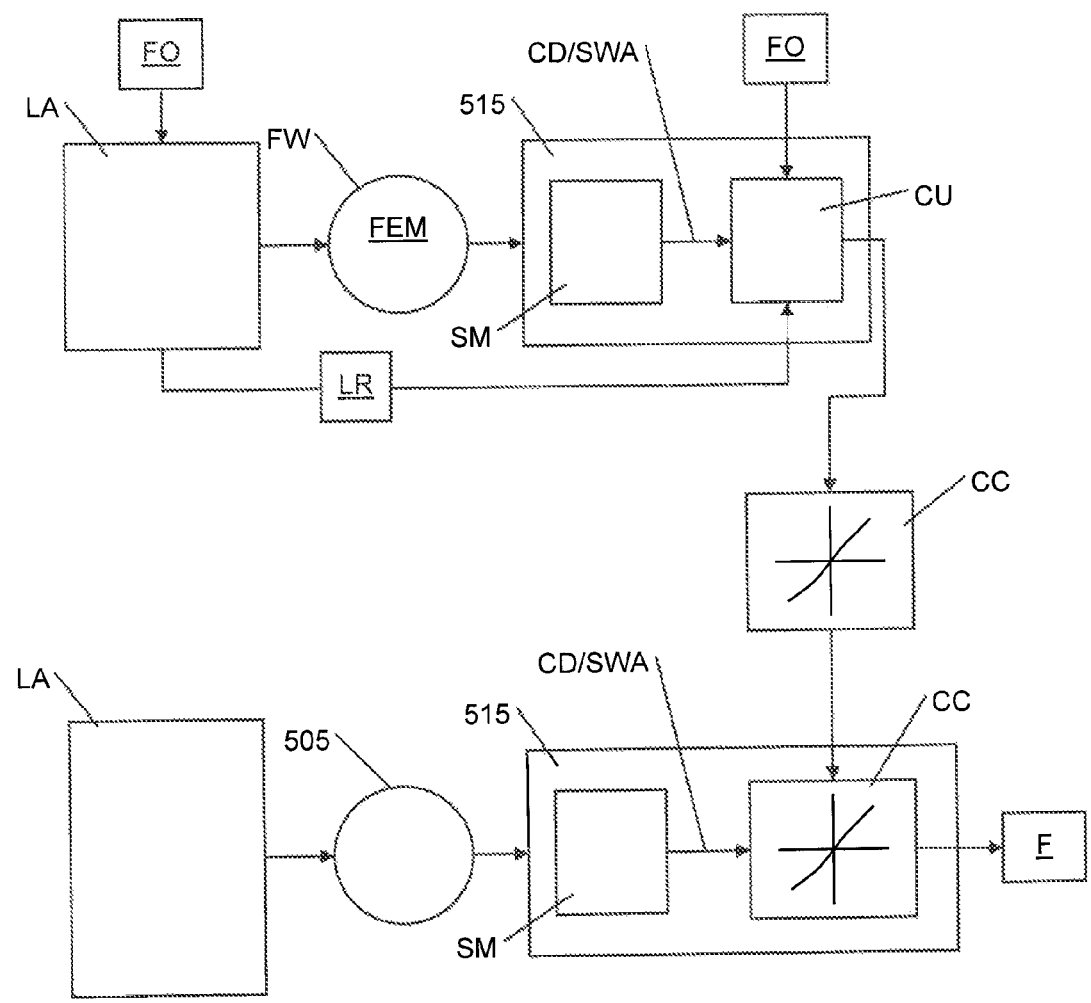
FIG. 16 illustrates the apparatus, according to an embodiment of the present invention.

FIG. 16 illustrates the apparatus according to an embodiment of the present invention that operates in accordance with the method described with reference to FIG. 12. The focus offsets FO are used by the scanner LA to expose the focus exposure matrix FEM on the FEM wafer FW. The FEM wafer is measured by the scatterometer SM in metrology tool 515. The CD/S WA results are passed to the calibration unit CU. The CU uses them with the focus offsets FO and the leveling residues LR obtained from the scanner LA to correct for the unflatness and generate a calibration curve CC. In the lower half of FIG. 16, the calibration curve CC is used in a monitoring flow such as loop 1 described with reference to FIG. 9 above. The scanner LA exposes a monitor wafer 505 that is measured by the metrology tool 515. The CD/SWA measurements are then used with the calibration curve CC to determine focus measurements F that can be used to control the operation of the scanner.

Figure 17:
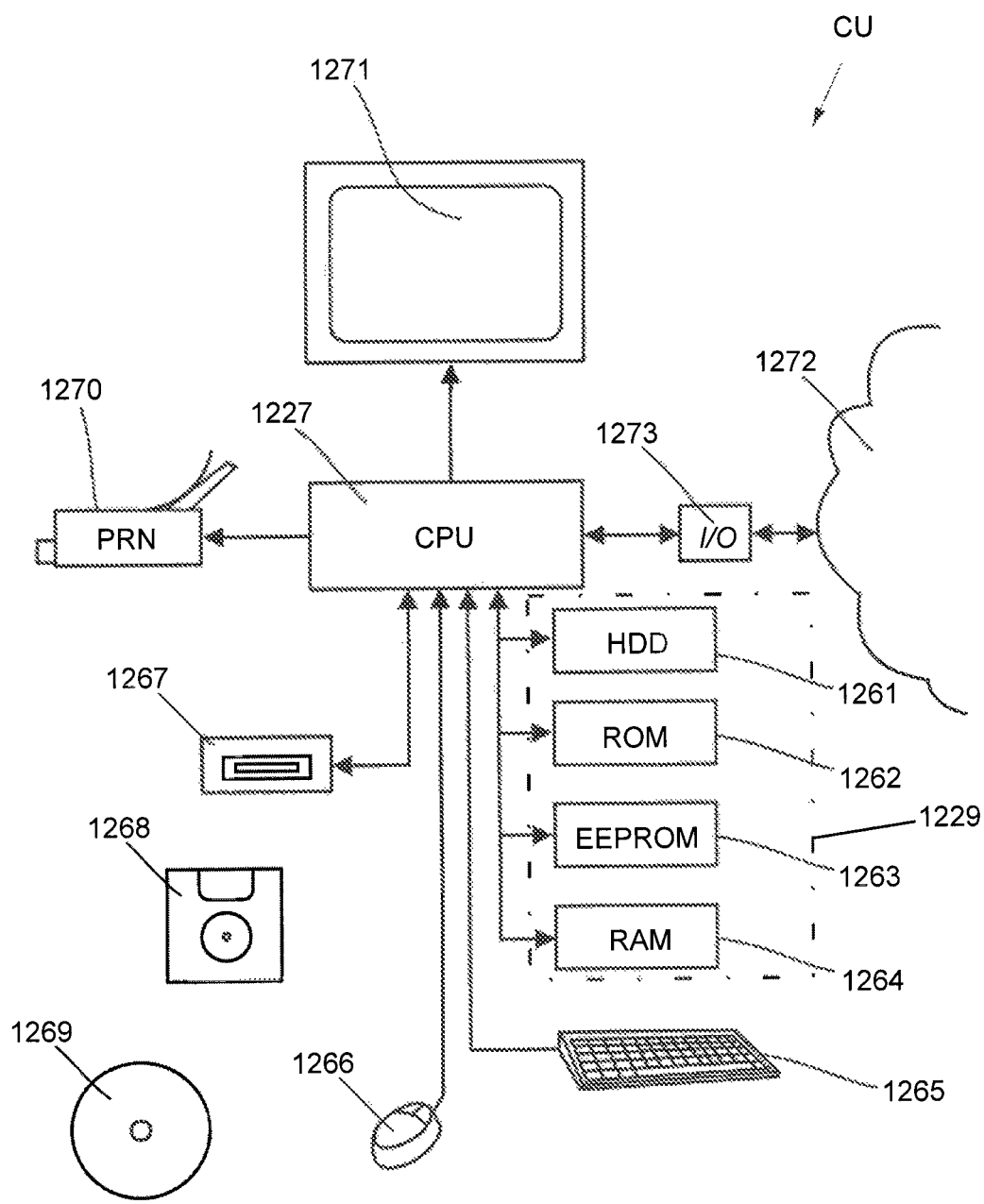
FIG. 17 illustrates a calibration unit controlling the apparatus and method, according to an embodiment of the present invention.

FIG. 17 illustrates a calibration unit controlling the apparatus and method according to an embodiment of the present invention. It should be understood that the calibration unit CU in the previous embodiments may be based on a computer assembly as shown in FIG. 14. The computer assembly may be a dedicated computer in the form of a control unit in embodiments of the assembly according to the present invention or, alternatively, be a central computer controlling the lithographic or inspection apparatus. The computer assembly may be arranged for loading a computer program product comprising computer executable code. This may enable the computer assembly, when the computer program product is downloaded, to implement the novel operations of the inspection apparatus, in accordance with the methods described above.

Memory 1229 connected to processor 1227 may comprise a number of memory components like a hard disk 1231, Read Only Memory (ROM) 1262, Electrically Erasable Programmable Read Only Memory (EEPROM) 1263 and Random Access Memory (RAM) 1264. Not all aforementioned memory components need to be present. Furthermore, it is not essential that aforementioned memory components are physically in close proximity to the processor 1227 or to each other. They may be located at a distance away The processor 1227 may also be connected to some kind of user interface, for instance a keyboard 1265 or a mouse 1266. A touch screen, track ball, speech converter or other interfaces that are known to persons skilled in the art may also be used.

The processor 1227 may be connected to a reading unit 1267, which is arranged to read data, e.g., in the form of computer executable code, from and under some circumstances store data on a data carrier, like a removable disc 1268 or a CDROM 1269. Also DVD's or other data carriers known to persons skilled in the art may be used.

The processor 1227 may also be connected to a printer 1270 to print out output data on paper as well as to a display 1271, for instance a monitor or LCD (Liquid Crystal Display), of any other type of display known to a person skilled in the art.

The processor 1227 may be connected to a communications network 1272, for instance a public switched telephone network (PSTN), a local area network (LAN), a wide area network (WAN) etc. by means of transmitters/receivers 1273 responsible for input/output (I/O). The processor 1227 may be arranged to communicate with other communication systems via the communications network 1272. In an embodiment of the present invention external computers (not shown), for instance personal computers of operators, can log into the processor 1227 via the communications network 1272.

The processor 1227 may be implemented as an independent system or as a number of processing units that operate in parallel, wherein each processing unit is arranged to execute sub-tasks of a larger program. The processing units may also be divided in one or more main processing units with several sub-processing units. Some processing units of the processor 1227 may even be located a distance away of the other processing units and communicate via communications network 1272. Separate processing units external to the lithographic apparatus may be used, for example, for implementing the scanner stability module 500, Advanced Process Control (APC) module 525 and Manufacturing Execution System (MES). These processing units can have the same general architecture as the one illustrated here.

It is observed that, although all connections in the drawing are shown as physical connections, one or more of these connections can be made wireless. They are only intended to show that "connected" units are arranged to communicate with one another in some way. The computer system can be any signal processing system with analogue and/or digital and/or software technology arranged to perform the functions discussed here.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the present invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents

The invention claimed is:

1. A method comprising:
    obtaining a plurality of surface level measurements of a substrate at a plurality of different level sensing locations across the substrate;
    determining a focus setting for an exposure field region in accordance with a plurality of the surface level measurements having level sensing locations corresponding to the exposure field region;
    exposing the exposure field region on the substrate with a focus offset defined with reference to the focus setting to produce a calibration pattern at a target location;
    obtaining a focus-dependent property measurement of the calibration pattern measured using an inspection apparatus; and
    calibrating the inspection apparatus using the focus-dependent property measurement, the focus offset and at least one of the plurality of surface level measurements having a level sensing location corresponding to the target location, the plurality of surface level measurments representing local focus deviations caused by unflatness of the substrate within the exposure field region at the time of exposing the calabration pattern.

2. The method of claim 1, wherein the obtaining, the determining, and the exposing are repeated for a plurality of exposure field regions and the calibrating uses the focus-dependent property measurement of each pattern of each exposure field region, the focus offset of each respective exposure field region and at least one of the plurality of surface level measurements having a level sensing location corresponding to each respective target location of each respective exposure field region.

3. The method of claim 1, wherein the calibrating comprises correcting the focus offset using at least one of the plurality of surface level measurements having a level sensing location corresponding to the target location.

4. The method of claim 3, wherein the correcting the focus offset comprises subtracting from the focus offset a difference between the focus setting and the at least one of the plurality of surface level measurements having a level sensing location corresponding to the target location.

5. An inspection apparatus comprising:
    a device configured to measure at least one focus-dependent property of a pattern applied to a substrate and to report a focus property of the pattern based on the at least one focus-dependent property measurement and a calibration curve,
    wherein the calibration curve has been obtained by measuring the focus-dependent property at a plurality of locations on a calibration substrate, each of the locations being within an exposure field on which a calibration pattern has been applied with a known focus offset across the exposure field, and
    wherein the calibration curve has been obtained based on the focus offset associated with the exposure field and local focus deviations caused by unflatness of a surface of the calibration substrate within the exposure field at a time of exposing the calibration pattern.

6. The inspection apparatus of claim 5, wherein the inspection apparatus is provided separately from a lithographic exposure apparatus, the inspection apparatus is configured to receive, from a lithographic apparatus, surface level measurements made at a plurality of locations within the exposure field on the calibration substrate at the time of exposure of the calibration substrate, in addition to receiving information of the focus offset applicable to the exposure field, the inspection apparatus being further configured to obtain the calibration curve by reference to the received surface level measurements.

7. The inspection apparatus of claim 6, wherein the inspection apparatus is configured to obtain the calibration curve by reference to a focus dependent property measured at least one target location, the focus offset in an exposure field at the at least one target location and at least one of the plurality of surface level measurements having a level sensing location corresponding to the at least one target location.

8. A lithographic apparatus comprising:
    an illumination optical system configured to illuminate a pattern;
    a projection optical system configured to project an image of the pattern on to a substrate; and
    an inspection apparatus comprising:
        a device configured to measure at least one focus-dependent property of a pattern applied to a substrate and to report a focus property of the pattern based on the at least one focus-dependent property measurement and a calibration curve,
        wherein the calibration curve has been obtained by measuring the focus-dependent property at a plurality of locations on a calibration substrate, each of the locations being within an exposure field on which a calibration pattern has been applied with a known focus offset across the field, and
        wherein the calibration curve has been obtained based on the focus offset associated with the exposure field and local focus deviations caused by unflatness of a surface of the calibration substrate within the field at a time of exposing the calibration pattern.

9. A lithographic cell comprising:

a coater configured to coat a substrate with a radiation sensitive layer;

a lithographic apparatus configured to expose an image onto the radiation sensitive layer of the substrate coated by the coater;

a developer arranged to develop the image exposed by the lithographic apparatus; and an inspection apparatus comprising:

a device configured to measure at least one focus-dependent property of a pattern applied to a substrate by projection lithography, and to report a focus property of the pattern based on the at least one focus-dependent property measurement and a calibration curve, wherein the calibration curve has been obtained by measuring the focus-dependent property at a plurality of locations on a calibration substrate, each of the locations being within an exposure field on which a calibration pattern has been applied with a known focus offset across the exposure field, and wherein the calibration curve has been obtained based on the focus offset associated with the exposure field and local focus deviations caused by unflatness of a surface of the calibration substrate within the field at a time of exposing the calibration pattern.

10. An article of manufacture including a non-transitory computer-readable storage medium having instructions stored there on for calibrating an inspection apparatus that, in response to execution by a computing device, cause the computing device to preform operations comprising:

obtaining a plurality of surface level measurements of a substrate at a plurality of different level sensing locations across the substrate;

determining a focus setting for an exposure field region in accordance with a plurality of the surface level measurements having level sensing locations corresponding to the exposure field region;

obtaining a focus-dependent property measurement of a calibration pattern. measured using the inspection apparatus, the calibration pattern produced at a target location by a lithographic apparatus exposing the exposure field region on the substrate with a focus offset defined with reference to the focus setting; and calibrating the inspection apparatus using the focus-dependent property measurement, the focus offset, and at least one of the plurality of surface level measurements having a level sensing location corresponding to the target location, the plurality of surface level measurements representing local focus deviations caused by unflatness of the substrate within the exposure field region at the time of exposing the calibration pattern.

* * * * *

UNITED STATES PATENT AND TRADEMARK OFFICE
CERTIFICATE OF CORRECTION

PATENT NO.        : 8,908,148 B2
APPLICATION NO.   : 13/181905
DATED             : December 9, 2014
INVENTOR(S)       : Geraets et al.

It is certified that error appears in the above-identified patent and that said Letters Patent is hereby corrected as shown below:

In the Claims

In column 17, line 55, claim 1, after "offset", please insert --,--.

In column 17, line 58, claim 1, after "level", please delete "measurments" and insert --measurements--.

In column 17, line 61, claim 1, after "the", please delete "calabiration" and insert --calibration--.

In column 18, line 43, claim 7, after measured, please insert --at--.

In column 18, line 64, claim 8, after "across", please insert --exposure--.

In column 20, line 14, claim 10, after "pattern", please delete ".".

Signed and Sealed this
Seventh Day of July, 2015

Michelle K. Lee
*Director of the United States Patent and Trademark Office*